United States Patent [19]

Elliott et al.

[11] 4,000,181
[45] Dec. 28, 1976

[54] α-CYANO-PHENOXYBENZYL CYCLOPROPANE CARBOXYLATE INSECTICIDES

[75] Inventors: Michael Elliott, Harpenden; Norman Frank Janes, Luton; David Allen Pulman, Caddington, all of England

[73] Assignee: National Research Development Corporation, London, England

[22] Filed: July 29, 1975

[21] Appl. No.: 600,186

[30] Foreign Application Priority Data

Aug. 12, 1974 United Kingdom ............ 35479/74

[52] U.S. Cl. ........................... 424/304; 260/465 D; 260/468 H; 424/305; 424/306

[51] Int. Cl.² .................. A01N 9/20; C07C 69/74; C07C 121/75

[58] Field of Search .............. 260/465 D, 468 H; 424/304, 305, 306

[56] References Cited
UNITED STATES PATENTS 3,666,789   5/1972   Itaya et al. .................... 260/468
3,835,176   9/1974   Matsuo et al. .................. 260/465

Primary Examiner—Lewis Gotts
Assistant Examiner—Dolph H. Torrence
Attorney, Agent, or Firm—Cushman, Darby & Cushman

[57] ABSTRACT

New insecticides are compounds of the formula

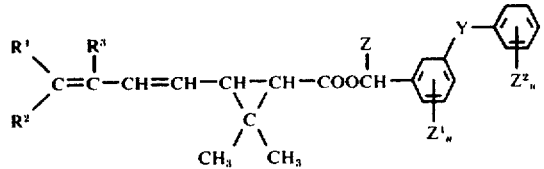

wherein two of $R^1$, $R^2$ and $R^3$ each represent methyl and the third represents hydrogen, Z represents H, $CH_3$—, —CN or —C≡CH, Y represents O or S, $Z^1$ and $Z^2$, which may be the same or different, each represent halogen or methyl, and $n$ is 0, 1 or 2.

6 Claims, No Drawings

α-CYANO-PHENOXYBENZYL CYCLOPROPANE CARBOXYLATE INSECTICIDES

This invention relates to insecticides and more particularly, to synthetic insecticides of the pyrethrin type, to their preparation, to compositions containing them and to the insecticidal use of the compounds and compositions.

For many years, research has been pursued in the field of synthetic analogues of the pyrethrins to discover synthetic substitutes having properties superior to those of the natural product. Research was initially directed to modifying the acid half and/or the alcohol half of the naturally occuring ester molecule to improve upon the toxicity or stability of the natural products while at the same time maintaining an acceptable balance of other relevant properties such as cost, ease of manufacture, low mammalian toxicity etc.

The present invention is directed to a new series of synthetic pyrethroids which are cheap to manufacture and are highly toxic to certain species of insects.

The present invention provides a compound of the general formula:

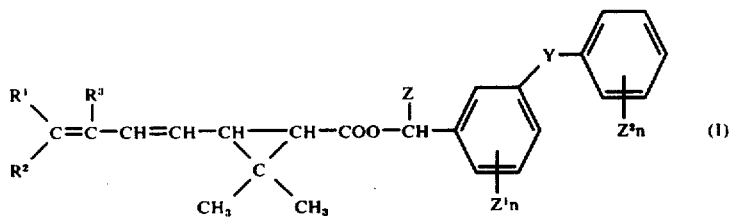 (I)

wherein two of $R^1$, $R^2$ and $R^3$ each represent a methyl group and the third represents hydrogen, Y= -O- or -S-, Z=H, $CH_3$, -CN or -C≡CH, $Z^1$, $Z^2$ which may be the same or different, each represent halogen e.g. chlorine, or methyl and $n = 0$, 1 or 2.

The esters of the present invention may be regarded structurally as esters of a 3-substituted-2,2-dimethyl cyclopropane carboxylic acid and an alcohol but while the esters may conveniently be described structurally in these terms, it will be appreciated and explained in more detail below, that the esters can be prepared by methods other than esterifying the acid with the alcohol and, in practice, normally are.

The acids from which the esters of the present invention are structurally derived are the 3-substituted-2,2-dimethyl cyclopropane carboxylic acids where the 3-substituent is a dimethylbuta-1,3-dienyl group.

The alcohols from which the esters of the present invention are structurally derived are essentially 3-phenoxy-benzyl and 3-phenylthio-benzyl alcohol which may be substituted on the α-carbon atom of the benzyl alcohol residue by a methyl group or by a cyano or ethynyl group. The alcohols may also be optionally substituted by up to 2 chlorine and/or methyl groups in either or both of the aromatic rings.

Specific alcohols from which the esters of the invention may be structurally derived include 3-phenoxy-benzyl alcohol, α-cyano-3-phenoxy-benzyl alcohol, α-ethynyl-3-phenoxy-benzyl alcohol, α-methyl-3-phenoxy-benzyl alcohol, 3-phenylthio-benzyl alcohol and α-cyano-3-phenylthio-benzyl alcohol.

The esters of the present invention exhibit geometrical and optical isomerism and consequently may be prepared in optically active forms which may subsequently be mixed together or as racemic mixtures which may be subsequently resolved into optically active forms. Optically active forms or racemic mixtures can be separated into the individual geometrical isomers. In addition to the geometrical isomerism that results from the configuration of the substituents on the cyclopropane ring with respect to one another and the ring, and from stereoisomerism about the double bonds in the 3-substituent, there is also the possibility of optical isomerisation resulting from the asymmetry of the α-carbon atom of the benzyl alcohol residue when Z does not represent hydrogen.

The esters of the present invention may be prepared by esterification involving the reaction of a cyclopropane carboxylic acid or derivative thereof of formula II with an alcohol or derivative thereof of formula III:

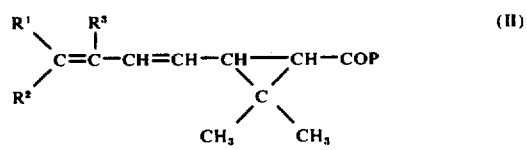 (II)

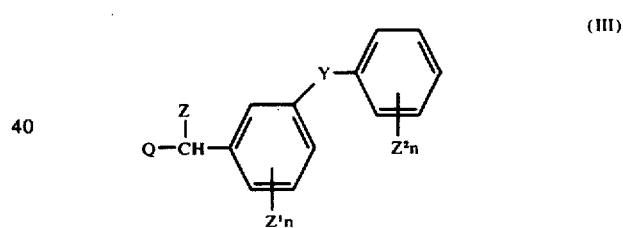 (III)

where Q and COP are functional groups or atoms which will react together to form an ester linkage and $R^1$, $R^2$, $R^3$, Y, Z, $Z^1$, $Z^2$ and n are as defined above.

It is usually convenient in practice either to react the acid or an acid halide with the alcohol, (COP=COOH or CO halide and Q = OH) or to react an halogen compound (Q = halogen) with a salt of the carboxylic acid (COP=COOM where M is, for example, a silver or triethyl-ammonium cation.

Alternatively, the esters may be prepared by a transesterification procedure using a lower alkyl ester of the acid, (COP = COO alkyl where the alkyl group contains 1 to 4 carbon atoms) and an alcohol III where Q = OH. The trans-esterification may be base catalysed and is a convenient procedure to adopt when, as will be discussed in more detail below, the carboxylic acid derivative II is prepared in the form of a lower alkyl ester.

The acids of formula II (COP = COOH), like the alcohols of formula III (Q = OH) are known compounds. We have found that the acids of formula II may be conveniently prepared by a Wittig reaction involving a phosphorane or ylide of formula IV and caronaldehyde of formula V or a lower alkyl ester thereof.

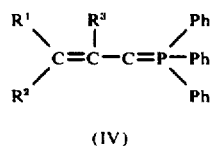 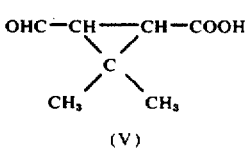

(IV)    (V)

The triphenyl substituted phosphoranes of formula IV are described in the chemical literature. It is preferred to use triphenyl phosphoranes as the stability of the triphenyl phosphorus oxide which is formed as a by product in the Wittig reaction is particularly high and this favours the completion of the Wittig reaction but any other organic group can, in principle, be used in place of the phenyl group.

The caronaldehyde or esters thereof may be prepared by ozonolysis of chrysanthemic acid or esters thereof respectively. When the caronaldehyde is prepared in the form of an ester or in the form of the free acid in trans-configuration, the reactant is of formula V as shown. However, if it is desired to use the free acid in the form of the cis-isomer, this is most conveniently reacted as its internal hemiacylal form. During the Wittig reaction, the hemiacylal ring opens and the aldehyde function the participates in the Wittig reaction to give the Wittig product but in cis-form.

The phosphorane IV and aldehyde V or its lower alkyl ester are preferably reacted in substantially equimolar proportions, conveniently in a solvent, e.g. an aromatic hydrocarbon such as benzene or a polar solvent such as dimethyl sulphoxide or tetra-hydrofurane or a chlorinated hydrocarbon such as dichloromethane. The product can be improved if the reaction is carried out in an inert atmosphere, e.g. under nitrogen.

The acids of formula II can also be prepared by the more traditional diazoacetate synthesis reacting 2,7-dimethyl-octa-2,4,6-triene or allo-ocimene(2,6-dimethyl-octa-2,4,6-triene) with ethyl diazoacetate e.g. in the presence of a copper catalyst. Reaction of the first mentioned triene proceeds with the formation of the desired ethyl 3-(4-methylpenta-1,3-dienyl)2,2-dimethyl cyclopropane carboxylate in high yield but allo-ocimene, because of its unsymetrical structure gives rise to a mixture of cyclopropane carboxylates.

The esters of the present invention can also be directly prepared by a Wittig reaction of the type described above. In this modification, the phosphorane IV is reacted with an ester of caronaldehyde of formula VI where Y, Z, Z¹, Z² and n are as defined above.

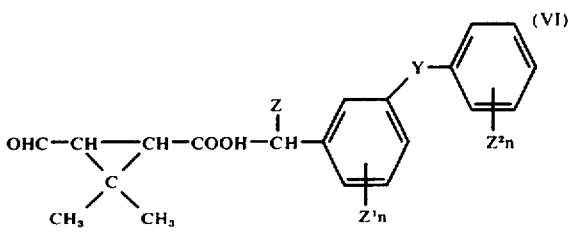

The esters of formula VI may be prepared either by esterifying caronaldehyde or an esterifiable derivative thereof with an alcohol or esterifiable derivative thereof of formula III or by ozonolysis of the appropriate ester of chrysanthemic acid.

Alcohols of formula III where Z represents CN or C≡CH or CH$_3$ can be prepared by conventional methods from the corresponding aldehydes. Thus, the desired 3-phenoxy or 3-phenyl-thio-benzaldehyde can be reacted with (a) HCN, conveniently generated in situ from KCN and acid, when addition of HCN occurs forming the cyanhydrin or (b) a metal acetylide derivative or an acetylenic or alkyl Grignard reagent.

One or more of the insecticidal esters of the invention may be formulated with an inert carrier or diluent to give insecticidal compositions and these may be prepared, for example, in the form of dusts and granular solids, wettable powders, mosquito coils and other solid preparations or as emulsions, emulsifiable concentrates, sprays and aerosols and other liquid preparations after the addition of the appropriate solvents, diluents and surface active agents.

Pyrethrum synergists such as piperonyl butoxide or tropital may be added to these compositions. The insecticidal compositions may also include naturally occurring or other known synthetic pyrethrins to improve kill and/or knock-down or to synergise the activity of the pyrethrins in the compositions.

The new esters of the invention or insecticidal compositions containing them may be used for controlling insects on a domestic or agricultural scale by treating the insects themselves or an environment susceptible to insect attack with the compounds or compositions of the invention.

The following Examples are given to illustrate the invention. Temperatures are in °C. Refractive indices are measured at 20° C.

EXAMPLE 1 a.

t-Butyl(+)trans-3-(4-methylpenta-1,3-dienyl)-2,2-dimethylcyclopropenecarboxylate 3-Methylbut-2-enyltriphenylphosphonium bromide (8.3 g was added slowly under nitrogen to a stirred suspension of sodamide in liquid ammonia (from sodium (0.6 g) and ammonia (100 ml)). The ammonia was allowed to evaporate and benzene (100 ml) added. The mixture was heated at reflux for 30 minutes, cooled, and decanted. The benzene solution of the phosphorane was added dropwise under nitrogen to a stirred solution of t-butyl(+)trans-caronaldehyde (1.3 g). Stirring was continued for a further 30 minutes when the solvent was removed in vacuo. The residue was extracted with ether, washed with water and dried (Na$_2$SO$_4$). Evaporation yielded a solid which was extracted with light petroleum and evaporated to give the title liquid (b.p. 90°/0.8 mm) yield = 0.76 g; n$_d$ = 1.4960.

b.

(+)-3-Phenoxy-α-cyanobenzyl(+)-trans-3-(4-methylpenta-1,3-dienyl)-2,2-dimethyl cyclopropane carboxylate The t-butyl ester (0.28 g) from (a) above, toluene-4-sulphonic acid (50 mg) and benzene (5 ml) were refluxed for 2 hours and cooled to give a solution of the corresponding carboxylic acid. Pyridine (114 μl) and thioyl chloride (100 μl) were added to the carboxylic acid solution and the solution left to stand for 3 hours. The resulting acid chloride was treated with a solution of pyridine (90 ul)(+)-3-phenoxy-α-cyanobenzyl alcohol (270 mg) in benzene (5 ml), allowed to stand overnight, the solvent evaporated and the residue chromatographed on neutral alumina using benzene as solvent to give the title ester (240 mg); $n_d = 1.5649$. This compound is designated compound P28A.

EXAMPLE 2 a.
(+)-cis-3-(4-methylpenta-1,3-dienyl)-2,2-dimethylcyclopropanecarboxylic acid

The phosphorane described in Example 1 was added dropwise to a stirred benzene solution of the internal hemi-acylal of (+)cis-caronaldehyde acid (0.9 g) under nitrogen, stirring being continued for a further 30 minutes. The solvent was removed and water added to the residue, which was extracted with ether. The ethereal solution was extracted with 5% sodium hydroxide solution and the aqueous phase combined with the original aqueous solution. Acidification of the combined solutions followed by extraction with dichloromethane yielded the title acid after drying ($Na_2SO_4$) and evaporation.

b.
(+)-3-Phenoxy-α-cyano-benzyl(+)cis-3-(4-methylpenta-1,3-dienyl)-2,2-dimethyl-cyclopropane carboxylate The solution of the acid prepared in (a) above (80 mg) in benzene (3 ml) was treated with pyridine (34 μl) and thionyl chloride (30 μl) and left to stand for 3 hours, when the corresponding acid chloride had formed. A solution of (+)-3-phenoxy-α-cyanobenzyl alcohol (102 mg) and pyridine (34 μl) in benzene (2 ml) was added to the acid chloride and the mixture left to stand overnight at room temperature. Chromatography on neutral alumina using benzene as eluent yielded, after evaporation, the title ester (100 mg); $n_d = 1.5527$. This compound is designated P28B.

EXAMPLE 3

3-Phenoxybenzyl(+)trans-3-(4-methylpenta-1,3-dienyl)2,2-dimethyl cyclopropane carboxylate The t-butyl ester prepared in Example 1 (0.28 g), toluene-4-sulphonic acid (50 mg) and benzene (5 ml) were refluxed for 2 hours and cooled to give the corresponding acid. Pyridine (1411 μl) and thionyl chloride (110 μl) were added and the mixture left to stand for 3 hours to give the corresponding acid chloride. Treatment of the acid chloride, with a solution of pyridine (90 μl), 3-phenoxybenzyl alcohol (240 mg) in benzene (5 ml), gave, after standing overnight, followed by the work up procedure of Examples 1 and 2, the title ester (270 mg); $n_d = 1.5695$. This compound is designated P28C.

EXAMPLE 4

1. Addition of ethyl diazoacetate to allo-ocimene

Ethyl diazoacetate (15 g) in allo-ocimene (18 ml) was added to a stirred mixture of allo-ocimeme (17 ml) and copper sulphate (0.3 g) at 80° during 1½ hours. The mixture was distilled to give unreacted allo-ocimene, then, at 79° – 106°/0.4 mm, the mixture of ethyl cyclopropane carboxylate (14.3 g), $n_d^{20} = 1.5041$. This mixture includes the ethyl ester of formula:

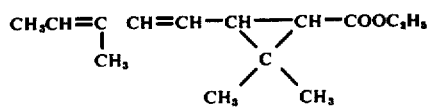

2. Transesterification

To a solution prepared by dissolving sodium (40 mg) in 3-phenoxybenzyl alcohol (2.0 g) and toluene (20 ml) was added the mixture of ethyl esters (2.0 g) from (1) above under nitrogen at 110° C. After 30 minutes, the mixture was chromatographed on alumina, eluting with benzene. Evaporation gave a liquid residue which includes the ester of formula:

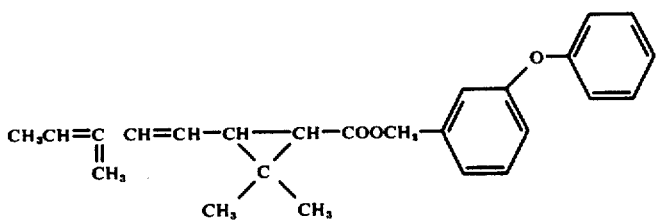

The insecticidal activity of the new compounds against mustard beetles (Phaedon cochleariae Fab.) was tested by applying acetone solutions of the test compound ventrally to adult insects using a micro drop applicator. The treated insects were maintained for 48 hours after which time kill is assessed. Two replicates of 40–50 beetles were used at the dose level tested. Compound P28A produced a 98 % kill when used in a concentration of 0.0002% w/v. Compound P28B produced a 100% kill when used in a concentration of 0.0002% w/v. Compound P28C produced a 68% kill when used at the higher concentration of 0.002 % w/v. Bioresmethrin, (5-benzyl-3-furylmethyl (+)-trans-chrysanthemate), one of the most toxic pyrethroids to mustard beetles has $LD_{50}$ of 0.0005 w/v.

EXAMPLE 5

A. Addition of Ethyldiazoacetate to 2,7-dimethyl-octa-2,4,6-triene

Ethyldiazoacetate (6.3 grams) in 2,7-dimethyl-octa-2,4,6-triene (5 g) was added to a stirred mixture of the same dimethyloctatriene (5 g) and copper sulphate (0.2 g) at 80° C over 0.5 hours. The mixture was then distilled as described in Example 4 to give, at 112° – 122° C at 5 mm, a mixture of ethylcyclopropane carboxylates (5.9 g) having $n^{20}_D$ 1.4950. N.M.R. indicates that this mixture includes about 40% of the ethyl ester of the formula:

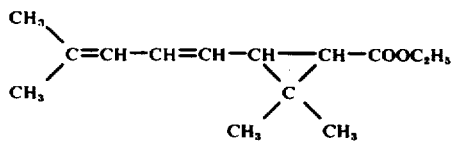

B. Transesterification

The mixture of ethylcyclopropane carboxylates was subject to transesterification by the procedure described in Example 4 (2) to give, after chromatography on alumina and eluting with benzene, a liquid residue which included the ester of formula

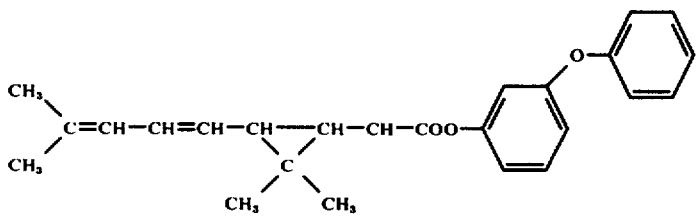

The insecticidal activity of the esters described in Example 1–3 was assessed against houseflies and mustard beetles by the following procedure:

HOUSEFLIES (*Musca domestica*)

Female flies were treated on the thorax with a 1 micro liter drop of insectide dissolved in acetone. Two replicates of 15 flies were used at each dose rate and 6 dose rates were used per compound a test. After treatment, the flies were maintained at a temperature of 20° C. + 1° and kill was assessed 24 and 28 hours after treatment. $LD_{50}$ values were calculated in micro grams of insecticide per fly and relative toxicities were calculated from the inverse ratios of the $LD_{50}$ values.

MUSTARD BEETLES (*Phaedon cochleariae Fab*)

Acetone solutions of the test compound were applied ventrally to adult mustard beetles using a micro drop applicator. The treated insects were maintained for 48 hours after which time kill is assessed. Two replicates of 40 – 50 mustard beetles were used at each dose level and 3 – 4 dose levels were used for each compound. Again, $LD_{50}$ values were calculated and relative toxicities were calculated from the inverse ratios of $LD_{50}$ values.

Relative toxicities were calculated by comparison with that of 5-benzyl-3-furylmethyl (+)-trans-chrysanthemate (bioresmethrin) which is one of the most toxic chrysanthemate esters known to houseflies and mustard beetles, its toxicity being about 24 times that of allethrin to houseflies and 65 times that of allethrin to mustard beetles. The following results were obtained.

| Compound | Relative Toxicities Houseflies | Mustard Beetles |
| --- | --- | --- |
| P28A | 100 | 30 |
| P28B | 150 | 40 |
| P28C | 13 | 23 |
| Bioresmethrin | 100 | 100 |

We claim:
1. A compound of the formula

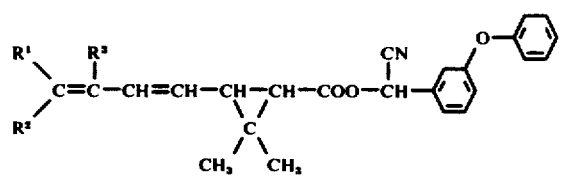

wherein two of $R^1$, $R^2$ and $R^3$ each represent methyl and the third represents hydrogen.

2. A compound according to claim 1, wherein $R^1$ and $R^2$ each represent methyl and $R^3$ represents hydrogen.

3. A compound according to claim 1, wherein $R^1$ and $R^3$ each represent methyl and $R^2$ represents hydrogen.

4. The compound according to claim 1, which is α-cyano-3-phenoxybenzyl 2,2-dimethyl-3-(4-methylpenta-1,3-dienyl)-cyclopropane carboxylate or; (+)-α-cyano-3-phenoxybenzyl (+)-cis-2,2-dimethyl-3-(4-methylpenta-1,3-dienyl)-cyclopropane carboxylate.

5. An insecticidal composition comprising a compound according to claim 1, together with an inert carrier or diluent.

6. A method for controlling the level of insect infestation which comprises applying to an insect or to an environment susceptible to insect attack, a compound according to claim 1.

* * * * *